US010101293B2

(12) United States Patent
Gupta

(10) Patent No.: US 10,101,293 B2
(45) Date of Patent: Oct. 16, 2018

(54) SENSING PLATFORM FOR TRANSDUCTION OF INFORMATION

(71) Applicant: The Board of Trustees of the Leland Stanford Junior University, Palo Alto, CA (US)

(72) Inventor: Chaitanya Gupta, Foster City, CA (US)

(73) Assignee: THE BOARD OF TRUSTEES OF THE LELAND STANFORD JUNIO, Palo Alto, CA (US)

( * ) Notice: Subject to any disclaimer, the term of this patent is extended or adjusted under 35 U.S.C. 154(b) by 726 days.

(21) Appl. No.: 14/455,205

(22) Filed: Aug. 8, 2014

(65) Prior Publication Data

US 2015/0041337 A1 Feb. 12, 2015

Related U.S. Application Data

(60) Provisional application No. 61/864,072, filed on Aug. 9, 2013.

(51) Int. Cl.
G01N 27/32 (2006.01)
G01N 27/327 (2006.01)
B01L 3/00 (2006.01)

(52) U.S. Cl.
CPC ........ *G01N 27/3278* (2013.01); *B01L 3/5027* (2013.01)

(58) Field of Classification Search
CPC ........... G01N 27/3271; G01N 27/3276; G01N 32/3278
USPC ....................... 324/693, 698, 71.1
See application file for complete search history.

(56) References Cited

U.S. PATENT DOCUMENTS

| 6,008,059 | A | 12/1999 | Schrier et al. |
| 7,470,352 | B2 | 12/2008 | Eversmann et al. |
| 9,285,336 | B2 | 3/2016 | Gupta |
| 2004/0120185 | A1* | 6/2004 | Kang ............... G01N 27/76 365/158 |
| 2008/0036444 | A1* | 2/2008 | Paulus ............. G01N 27/3276 324/71.1 |

(Continued)

OTHER PUBLICATIONS

Yoo et al. (Thin Solid Films, 518, 5986-5991 (Year: 2010).

*Primary Examiner* — Vincent Q Nguyen
(74) *Attorney, Agent, or Firm* — Thomas | Horstemeyer, LLP; Christopher B. Linder; Jason M. Perilla

(57) ABSTRACT

Aspects of a biosensor platform system and method are described. In one embodiment, the biosensor platform system includes a fluidic system and tunneling biosensor interface coupled to the fluidic system. The tunneling biosensor interface may include a transducing electrode array having at least one dielectric thin film deposited on an electrode array. The biosensor platform system may further include processing logic operatively coupled to the transducing electrode array. In operation, the application of an electromagnetic field at an interface between an electrode and an electrolyte in the system, for example, may result in the transfer of charge across the interface. The transfer of charge is, in turn, characterized by electromagnetic field-mediated tunneling of electrons that may be assisted by exchange of energy with thermal vibrations at the interface. By analysis of the transfer of charge, the identify of various analytes, for example, or other compositions.

15 Claims, 17 Drawing Sheets

(56) References Cited

U.S. PATENT DOCUMENTS

| | | | |
|---|---|---|---|
| 2011/0108422 A1* | 5/2011 | Heller | G01N 27/447 |
| | | | 204/547 |
| 2012/0091011 A1 | 4/2012 | Graham et al. | |
| 2012/0142026 A1 | 6/2012 | Miller et al. | |
| 2013/0051115 A1* | 2/2013 | En | H01L 27/0694 |
| | | | 365/148 |
| 2013/0158378 A1* | 6/2013 | Berger | A61B 5/14546 |
| | | | 600/348 |
| 2016/0161438 A1 | 6/2016 | Gupta | |

* cited by examiner

Planar micro-fabricated electrodes

Tip-based probes

Through-substrate vias

SENSING PLATFORM FOR TRANSDUCTION OF INFORMATION

CROSS-REFERENCE TO RELATED APPLICATIONS

This application claims the benefit of U.S. Provisional Application No. 61/864,072, filed Aug. 9, 2013, the entire contents of which application is hereby incorporated herein by reference.

STATEMENT REGARDING FEDERALLY SPONSORED RESEARCH OR DEVELOPMENT

This invention was made with government support under contract N66001-11-1-4111 awarded by the Defense Advanced Research Projects Agency. The government has certain rights in this invention.

BACKGROUND

In a variety of applications, the detection and identification of certain chemical or molecular species is desired. For example, it may be desirable to identify small molecule analytes, such as amino acids and metallic ions, as well as relatively large proteins, such as DNA and RNA. In particular, the detection of biomarkers in biological samples is important for disease detection, disease analysis, and disease pathway investigation. Further, the detection of contaminants in environmental samples, such as in water, is important for homeland security, public safety, and environmental welfare.

BRIEF DESCRIPTION OF THE DRAWINGS

For a more complete understanding of the embodiments described herein and the advantages thereof, reference is now made to the following description, in conjunction with the accompanying figures briefly described as follows.

Figure 1A:
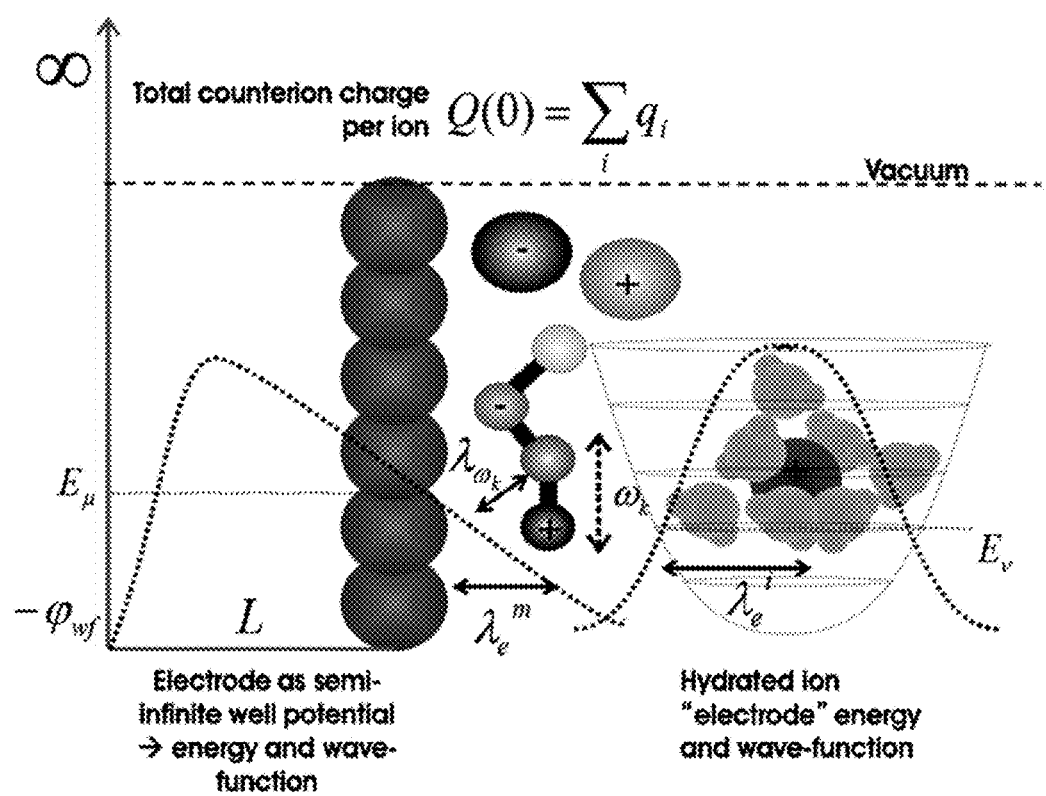
FIG. 1A illustrates an example schematic diagram of an electrochemical interface with characteristic length scales to determine the nature of a charge transfer reaction according to aspects of the embodiments.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION OF THE EMBODIMENTS

As described above, the detection and identification of certain chemical or molecular species is desired in various fields and applications. In particular, the detection of biomarkers in biological samples is important for disease detection, disease analysis, and disease pathway investigation. Further, the detection of contaminants in environmental samples, such as in water, is important for homeland security, public safety, and environmental welfare.

Using conventional means and methods, certain chemical and molecular species may be identified. The identification of these species may be achieved using bioassays, electronic systems, or combinations thereof, for example. Typically, a bioassay may indirectly detect analytes by measuring various molecular interactions. Some bioassays detect analytes by activating a label that is covalently attached to a binding partner upon analyte binding to a bait molecule. Other bioassays measure analyte binding of an immobilized bait molecule to a solid substrate and changes in charge, refractive index, or mass change at an interface between the solid substrate and liquid sample. In various forms, electronic systems may rely upon alterations in current, voltage, or charge to indirectly detect, qualify, and quantify chemical analytes. It should be appreciated, however, that the demand for a low-cost and field-use friendly means or method to identify and detect low concentration analytes has resulted in ongoing efforts to improve the functionality and practicality of chemical and molecular detecting devices.

A good platform for detecting biological threats should be able to identify a large range of agents and toxins. As many of these agents and toxins are highly infective, the platform should demonstrate sensitivity and specificity to allow early exposure detection, reduce false positives, enable targeted countermeasures, and minimize the spread of infection. The platform should also allow for rapid detection to enable timely intervention. In this context, the challenges of developing a sensitive, yet specific, high-throughput detector having a wide working range may be appreciated. The challenges are further complicated considering the need for portability, minimal operational complexity, low power consumption, low manufacturing cost, and operability in harsh environments, for example.

Platforms for detecting molecules have evolved from impractical and laboratory-based systems to portable miniaturized "Lab-on-a-Chip" platforms. For example, the detection of biological threats has evolved from conducting threat detection and diagnosis though the Laboratory Response Network to detection using a mobile lab based system, such as the Biological Integrated Detection System (BIDS), to mesoscale peptide bioassays. This evolution is representative of the need for small molecule detectors that are capable of rapid and point-of-use detection.

Traditional bioassays fall into two categories: label-based or label-free. In label-based bioassays, the target molecule, such as a toxin or other molecule, binds with a bait molecule, often a complementary peptide, DNA, or RNA molecule which has a covalently attached label. Fluorescent dyes and radioactive isotopes are commonly used labels where binding of the target molecule to the bait molecule causes the release of fluorescence or radiation. In this context, the measurement of fluorescence or radioactivity provides an indirect detection and quantification of the target molecule.

However, these array label-based assays suffer from significant limitations despite some improved sensitivity and specificity. First, these array label-based systems require identification, design, synthesis, and immobilization of the bait molecules, which are significantly rate-limiting in the assay manufacturing process. Second, immobilization of a bait molecule with a three-dimensional structure results in a loss of activity of the bait molecule which may generate a false negative outcome. Third, the addition of a covalently bound fluorophore or other radioactive tag significantly modifies an interaction between the target molecule and the bait molecule, resulting in false positives and negatives. Fourth, tagging a bait molecule with a fluorescing or radioactive tag adds a layer of complexity to the manufacturing process. Fifth, the assay requires that readers detect the optical/radiation signal from the tags be incorporated with the platform, thus dramatically increasing platform cost while reducing portability. Finally, the extinction of a signal generated from a binding event due to scattering from the background matrix is a persistent problem.

In the context outlined above, the limitations imposed by traditional label-based bioassays prompted the development of label-free methods. Like the label-based bioassays, a label-free bioassay includes bait molecules immobilized on a solid substrate. The detection of the binding between the target molecule and bait molecule is based on (a) the change in charge at the solid-liquid interface that results from the binding event, (b) evanescent wave attenuation due to a change in refractive index at the solid-liquid interface, and/or (c) mass change at the solid-liquid interface. Charge based detection methods eliminate the need for expensive signal readers, thereby reducing the cost of detection, enhancing system portability, reducing overall power consumption, and increasing ease of operation. The charge based method is also scalable, which is an essential strategy in developing a high throughput detection platform. Though the label-free platforms do not suffer from problems like tag-altered target molecule binding and reduced signal yield, they are still afflicted by the issue of bait molecule misfolding on immobilization to a solid surface.

Generally, the bait molecule is utilized to infer whether the target molecule is present or absent in both label-based and label-free platforms. The actual identity of the target molecule is inferred from the nature of the bait molecule with which binding occurs. Mass spectrometry, on the other hand, is a time-critical, broadband analysis technique that directly measures molecular composition from estimates of charge-to-mass ratios of vaporized fragments of the analyte. Commercial mass spectrometers are reportedly capable of detection in the nanomolar concentration range. Arrayed, multi-channel, modular architectures for time-of-flight (TOF) mass spectrometers have been detailed for rapid, in-parallel acquisition of information.

However, mass spectrometry analysis is better suited to larger molecular weight target molecules that can be fragmented into several constituent moieties for analysis. Small molecular weight (<5 kDa) target molecules are not easily identified by this technique. Mass spectrometer and associated ancillary equipment (e.g., vacuum pumps) are energy intensive in operation and are not easily miniaturized, thus making portability an issue. Additionally, mass spectrometer operation and data analysis require intervention of skilled technicians, making the detection platform ill-suited for point-of-use applications. Thus, in view of traditional detection systems, the need for a robust, rapid, low-cost, point-of-use detection platform for small amounts of molecules in fluid samples can be appreciated.

Molecular vibration-assisted-charge transfer between an electron source and donor has been documented in nature. Fruit flies detect odorants by transferring an electron from an intracellular electron source upon entrance of an odorant into a transmembrane pocket. The electron charge transfer stimulates G-protein mediated signal transduction pathways and thus allows the fruit fly to identify an odorant utilizing vibrational signatures of odorant molecules. Similarly, according to aspects of the embodiments described herein, the detection of molecular analytes by the detection of electron transfer is achieved. In the biosensor, according to the embodiments described herein, current measured due to electron transfer that contains information about vibrational frequencies of molecular bond vibrations within a molecular analyte, as well as information about participating electronic energies, is acquired directly from the engineered inorganic transducing interface and analyzed.

Generally, the biosensor system according to the embodiments described herein includes an electrochemical charge transfer platform where the application of an electromagnetic field at an interface between an electrode and an electrolyte results in the transfer of charge across the interface. The transfer of charge may occur from the electrode to a chemical species in the electrolyte that can accept the charge (i.e., a redox-active species) or vice-versa. The transfer of charge is, in turn, characterized by electromagnetic field-mediated tunneling of electrons that may be assisted by exchange of energy with thermal vibrations of other non-redox-active species (i.e., analytes) at the interface. The interface is engineered such that a number of collisions experienced by transferring electronic charge with other analyte molecules is minimal but not zero. The collisions of the tunneling electrons with thermal vibrations are responsible for the energy exchange between the transferring charge and the analyte molecules.

The electrochemical charge transfer platform according to the embodiments described herein includes a metal/semiconductor electrode and an organic or aqueous electrolyte separated by a thin dielectric layer. The organic or aqueous electrolyte, which is coupled or in immediate contact with the thin dielectric layer, is characterized by a distribution of uni-polar charge that decays to zero as distance from the dielectric-electrolyte interface increases. The dielectric layer acts as a molecular insulator that slows down the rate of electron transfer sufficiently such that a tunneling electron minimally collides with surrounding thermal vibrations. Measured current that would characterize the tunneling of electrons across a suitably engineered interface would contain signatures of the resonant energy exchange between the tunneling electrons and the molecular vibration modes of the analytes, as well as signatures of the electronic energies in the electrode and redox active species that participate in the tunneling process.

The biosensor system according to the embodiments described herein further includes a high gain noise suppression feedback loop to electronically "cool" the system and minimize thermal noise that otherwise dissipates the resonant signal of interest. At low electronic temperatures, transfer of electronic charge occurs in a resonant manner by inelastic interactions with quantized vibrations of a target analyte as well as by direct elastic interactions between the participating electronic energy levels.

In various aspects and embodiments, the biosensor system measures at least one of resonant interactions by measuring a) the tunneling current (I) as a function of applied voltage (V), b) small signal conductance (dI/dV) as a function of applied voltage, or c) conductance derivative ($d^2I/dV^2$) as a function of applied voltage. Each resonance feature manifests as a discontinuity in the measured profiles and may be correlated to a vibrational frequency of a molecular bond in the analyte or to a participating electronic energy level. Since vibrational frequencies may be relied upon as characteristic signatures of molecular bonds, akin to human fingerprints, for example, the number and types of bonds in the analyte can be determined from these discontinuities. Discontinuities corresponding to electronic energy levels yield information specific to the electronic structures of the electrode and electrolyte phases that may themselves be perturbed by the analyte chemistries. Each analyte possesses a unique molecular bond signature, thus allowing direct, highly specific analyte detection.

With further regard to resonant electron transfer at an electrochemical interface, the biosensor system described herein relies in part upon measuring electron flux produced in charge-transfer-related quantum-mechanical transitions at an electrochemical interface. In this context, the measured electron flux or currents are representative of molecular structural and chemical information where quantum mechanical transitions manifest as discontinuous features in the currents. The molecular structural and chemical information, once determined, is unique to each analyte, thus allowing for highly specific molecular species determination.

Turning now to the drawings, the features and aspects of the embodiments are described in further detail.

FIG. 1A illustrates an example schematic diagram of an electrochemical interface with characteristic length scales to determine the nature of a charge transfer reaction according to aspects of the embodiments. Charge transfer across an electrified electrode-electrolyte (or electrode-insulator-electrolyte) interface may be limited by several factors, such as a) mass transport of reactants to the electrode-electrolyte interface, b) capacitive charging/discharging of the electrode-electrolyte interface, or c) quantum-mechanical tunneling of electrons from electrode to redox energy levels or vice-versa. When the electrochemical interface is engineered such that charge transfer is limited by the electronic transition process, the nature of the electron transition and the magnitude of the transition charge flux depends on the extent of electronic coupling between the initial and final electronic energy states of the transferring electron as well as the strength of the nuclear-electrostatic coupling between the electron and the thermal molecular vibrations.

Figure 1B:
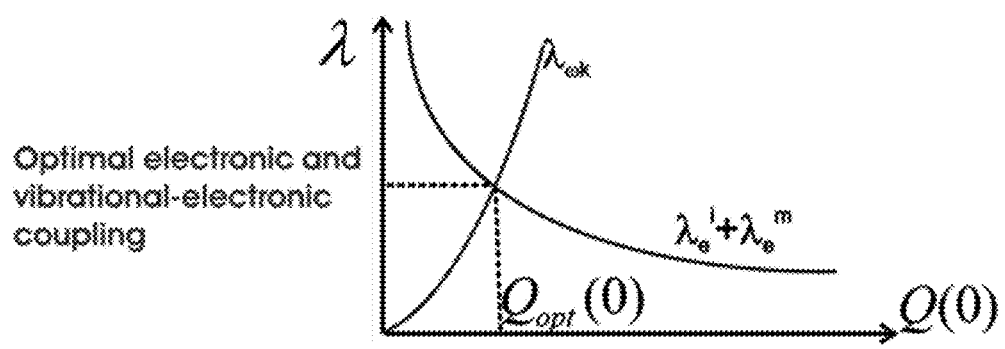
FIG. 1B illustrates an example regime, as an interface charge density, within which transduction of molecular vibration modes is possible according to aspects of the embodiments.

The strength of the coupling factors can be well represented by equivalent length scales. For differing values of length scale parameters, the nature of the transition process is qualitatively depicted in FIG. 1A. Length scale parameters are themselves depicted as functions of interface charge density Q(0) and, thus, the nature of the transition process can be modulated by active control of the interface charge density. One optimal charge transfer regime suitable for the transduction of vibrational mode information from the electron tunneling process relies upon an "intermediate" strength of the two coupling energies and hence an "intermediate" value of interface charge density, as depicted in FIG. 1B.

The electronic and electronic-nuclear coupling strengths can be tuned in many different ways, for example, by changing the applied electrostatic field, by tuning the local interface chemistry, conditioning the physical system to reduce its intrinsic noise, scaling down the physical sensor interface, and combinations thereof. In addition, assisting electromagnetic fields (e.g., optical and magnetic fields) may also be relied upon to induce electronic transitions between energy levels in the electrode-electrolyte system that are resonant with the dissipated energy of the field. Control of the above mentioned parameters reduces thermal de-phasing of the resonance phenomena in the charge transfer process.

Figure 2A:
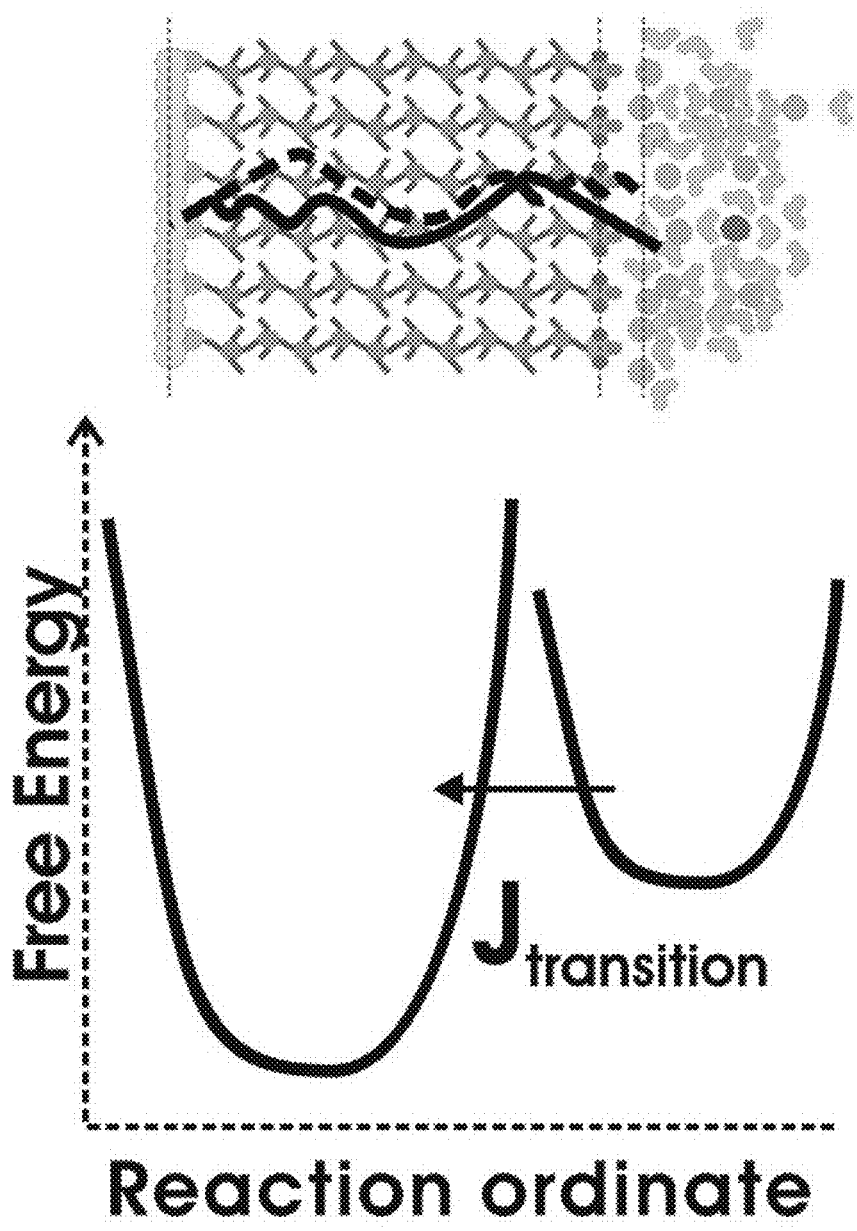
FIG. 2A illustrates an example of weak coupling between electronic energy and nuclear-vibrational states.
Figure 2B:
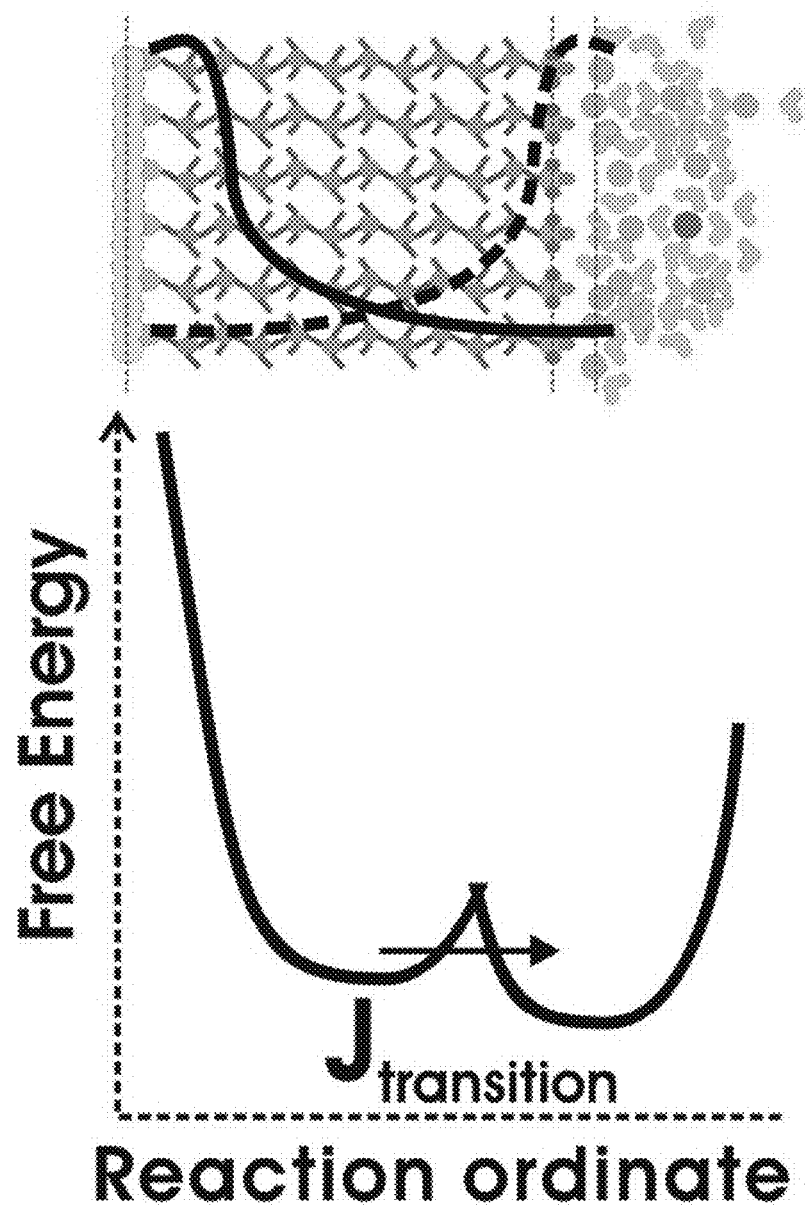
FIG. 2B illustrates an example of strong coupling between electronic energy and nuclear-vibrational states.

The coupling between electronic energy states participating in the transition process and the surrounding bath of thermal vibrational modes can be weak, as illustrated by the example in FIG. 2A, or strong, as illustrated by the example in FIG. 2B. Further, coupling strength may be tuned by applied bias, interface chemistry, interface size, intrinsic interface noise, the application of electromagnetic fields, or combinations thereof, for example. As illustrated in FIG. 2B, when an applied bias allows for electron transition where electronic energies are significantly coupled to vibrational modes, de-phasing is strong. In a strongly coupled electron transfer, the electron wavefunction is localized to initial and final energy states before and after the charge transition. As illustrated in FIG. 2B, this results in particle-like behavior and a thermalized non-adiabatic charge transfer event. On the other hand, in the case of weak coupling between the electronic energy states and the molecular vibrational energy levels, the electronic wavefunction is delocalized over initial and final electronic energy states. As illustrated in FIG. 2A, this results in a wave like interaction of the electron with the surrounding vibrational modes and enables the resonant transduction of vibrational mode information.

Figure 2C:
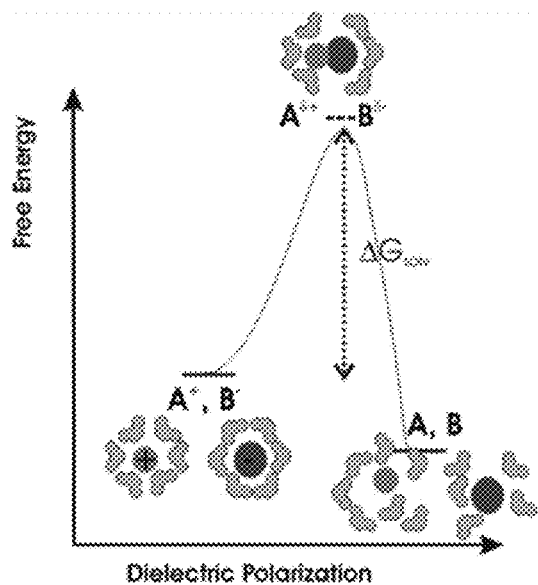
FIG. 2C illustrates an example reaction free energy schematic for an adiabatic reaction case when an electron source and donor (initial and final electronic energy states) are strongly coupled according to aspects of the embodiments.
Figure 2D:
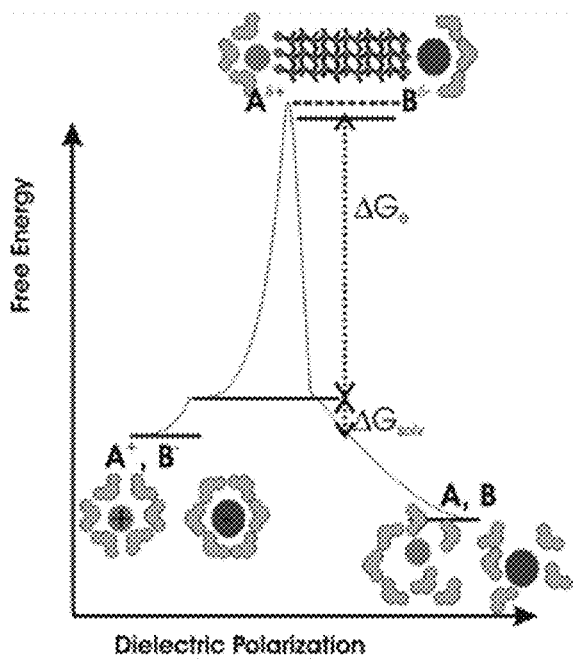
FIG. 2D illustrates an example reaction free energy schematic for a non-adiabatic reaction case when initial and final electronic energy states are weakly coupled according to aspects of the embodiments.

The coupling between the discrete electronic energy states of the electrode and the redox-active species in the electrolyte also affects the ability of the interface to transduce the molecular vibrational mode information. A strong coupling between the electrode-electrolyte energies results in a "fast" charge transfer event that is limited only by the rate of dielectric thermal repolarization around the electrode and redox-active species, as illustrated by the example in FIG. 2C. Importantly, for this kind of charge transfer reaction, referred to as an "adiabatic" reaction, the transitioning electron is always in a ground state resulting in no possibility for resonant electron transfer to occur. On the other hand, for the case where the coupling between electrode and electrolyte levels in very weak, there is little interaction between the two phases of the system and charge transfer is yet again mediated by thermal excitation only, as illustrated by the example in FIG. 2D.

An optimum level of electronic-electronic and electronic-nuclear coupling is required to transduce the discrete vibrational mode information as indicated previously. Thus, in the optimal case, the electron transfer is limited by the rate of the electronic tunneling transition from reactant to product state, where the electron participates in an inelastic exchange of energy with the molecules in the intervening layer between the electrode and redox active species in the electrolyte. This optimally-coupled transition allows the transferring electron to be de-excited from a higher energy level to a lower energy level, thereby losing energy to the intervening molecular species, which shows as a signature in the current, conductance, or conductance derivative signal.

Figure 3:
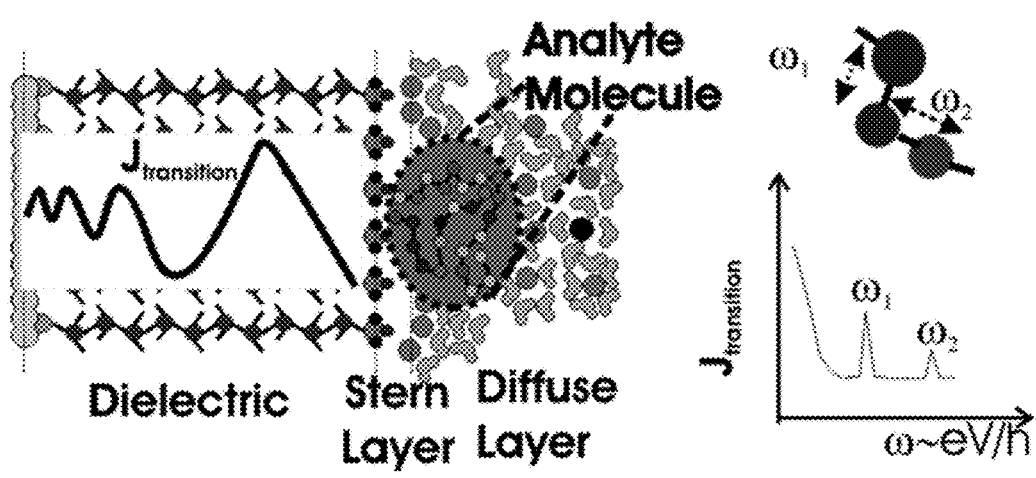
FIG. 3 illustrates an example schematic depicting the measurement of a flux of electrons crossing an electrified dielectric monolayer modified electrochemical interface and the interaction of the tunneling electrons with an analyte co-located at the interface according to aspects of the embodiments.

With regard to the design of a vibrational mode information transduction interface, according to aspects of the embodiments described herein, the measurement of the flux of electrons crossing an electrified dielectric monolayer modified electrochemical interface allows for analyte detection. In this context, FIG. 3 illustrates an example schematic depicting the measurement of a flux of electrons crossing an electrified dielectric monolayer modified electrochemical interface and the interaction of the tunneling electrons with an analyte co-located at the interface according to aspects of the embodiments.

In one embodiment described herein, a sensor consists of an electrode (e.g., metal/semiconductor), a molecularly thin spacer layer, and a redox-active species in the electrolyte. An electrode that acts as a source or sink of transitioning electrons may be defined by discrete electronic energy states that can interact with discrete energy levels of the molecular redox species in the electrolyte, as opposed to a continuous collection of energy levels that are characteristic of a macroscopic wire. The need for a discretized energy structure of the electrode at room temperature tends to the need for an electrode of nanoscale dimensions. The nanoscale electrode would, in turn, be electrically addressed by a lead (e.g., electrical lead) that applies or supplies a suitable voltage and, as a result, charge flows in an external instrumentation circuit as a tunneling current.

The sensor size, lead area, dielectric spacer thickness, choice of electrolyte (e.g., aqueous, organic, ionic salt), and choice of redox-active species in the electrolyte may be determined, for example, so as to optimize the electronic and electronic-nuclear coupling at the electrochemical interface. Quantitatively, "optimal" is defined in this context by a specific value of interface charge density. This value of interface charge density may be determined by kinetics of the accompanying electron transfer reaction (which determines the nature of electrode material, the nature of electrolyte, and type of redox active ion in the electrolyte) and dielectric spacer thickness. The determination of equivalent or suitable lead area is a trade-off between minimizing parasitic capacitance from insulated leads and electrical double layer at the solid-liquid interface and minimizing the thermal broadening of the discrete electronic energies of the nano-electrode with increasing size.

Figure 4:
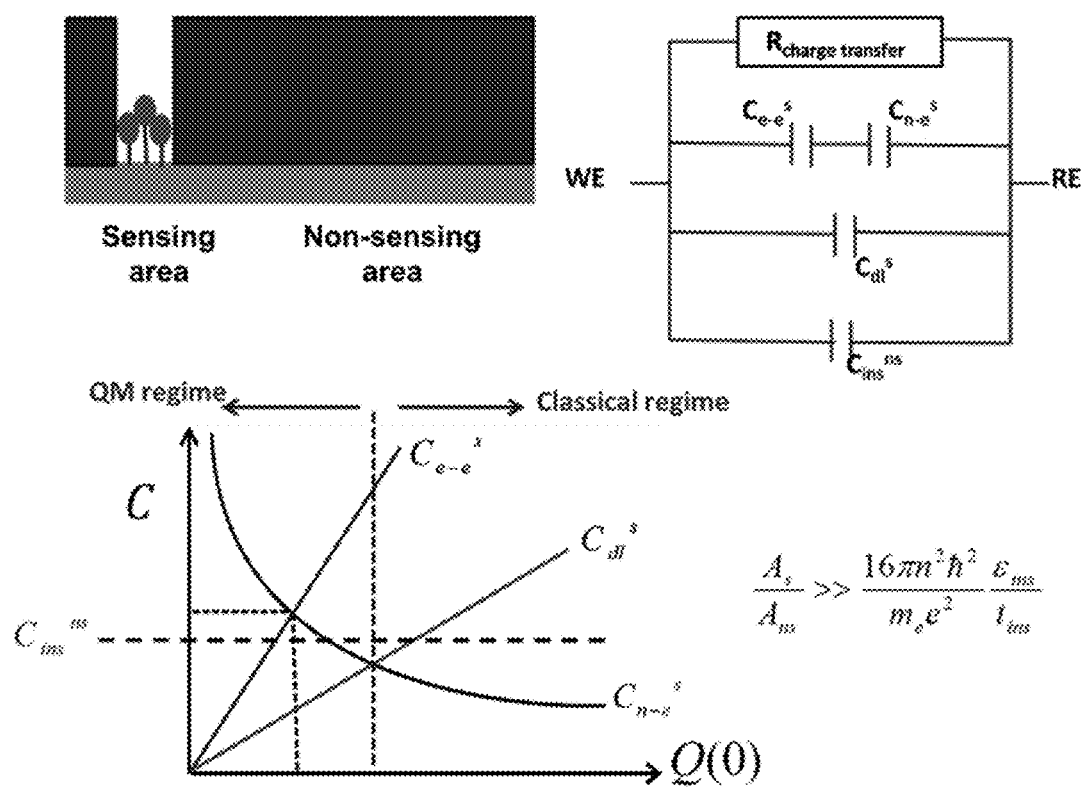
FIG. 4 illustrates example design considerations for a transducing interface and factors in view of quantum-mechanical to classical transition behavior according to aspects of the embodiments.

FIG. 4 illustrates design considerations for a transducing interface and factors in view of quantum-mechanical to classical transition behavior. As shown in FIG. 4, the total sensing area as well as the sensing to lead area ratio may be designed in view of the quantum-mechanical to classical transition behavior of the system as well as the transition between weak and strong nuclear-electronic coupling regimes. Additionally, a constraint on the upper value of the lead area is determined by estimating the extent of thermal broadening induced by a macroscopic lead that electrically addresses the nanoscale electrode. In some embodiments, an intervening molecularly insulating spacer may be utilized to weakly couple the macroscopic lead to the nanoscale electrode. At least in part, the choice of spacer material and dimensions and the total lead area determines or bears upon the effective broadening of the electronic energies of an electron in the nanoscale electrode. Thus, a suitable mix of these parameters may be chosen among embodiments to ensure that thermal broadening is below the thermal energy at room temperature (~25 meV). The electron flux or tunneling current at this nano-structured interface is measured either directly as a current or as an impedance/derivative of system impedance with applied voltage. In this context, by the application of suitable data analysis techniques, detailed structural information about a molecular analyte can be obtained.

With the application of a voltage between a macroscopic lead and a reference electrode that sits in bulk electrolyte solution, electrons tunnel from the nanoscale electrode to the redox-active species in the electrolyte. If the interface is engineered appropriately, for "optimal" coupling conditions, such that the tunneling of the electron from electrode to electrolyte is rate limiting and no other process (e.g., mass transfer of redox-active species to interface from bulk electrolyte, capacitive charging/discharging of interface charge, or tunneling of electrons from lead to nanoscale electrode) is slow enough to compete, then a current measured by a low noise transimpedance amplifier and acquired by a data acquisition system corresponds to a direct measurement of this tunneling event.

In other words, as an electron tunnels across the appropriately engineered interface, it loses energy equivalent to the applied bias value, and this energy is lost to molecular vibrations of analyte species with suitable vibrational energies that exist at the interface between the electrode and redox-active species. Thus, the biosensor according to the embodiments described herein measures a spectrum of molecular vibrational oscillation modes of an analyte at an electrochemical interface within a liquid electrolyte in resonance with an energy gap between initial and final electronic energy states of the electrochemical interface. In addition to vibrational signatures, the tunneling electron also transduces information about electronic resonances arising from elastic (i.e., collision-less) transitions between the electrode and redox species energy levels. However, it is expected that elastic transitions would be probabilistically less likely for a suitably designed interface.

In one sense, this approach is analogous to that of electromagnetic probes, such as near-infrared (NIR) vibrational spectroscopy probes, than with conventional electrostatic measurements. However, as the molecular structure information is transduced directly to an electronic signal before acquisition, the proposed biosensor is highly scalable. The direct acquisition of chemistry specific information about an analyte in the form of molecular vibrational modes also eliminates the need for time and labor-intensive combinatorial screening against bait-molecule probes required by traditional bioassays.

Figure 5:
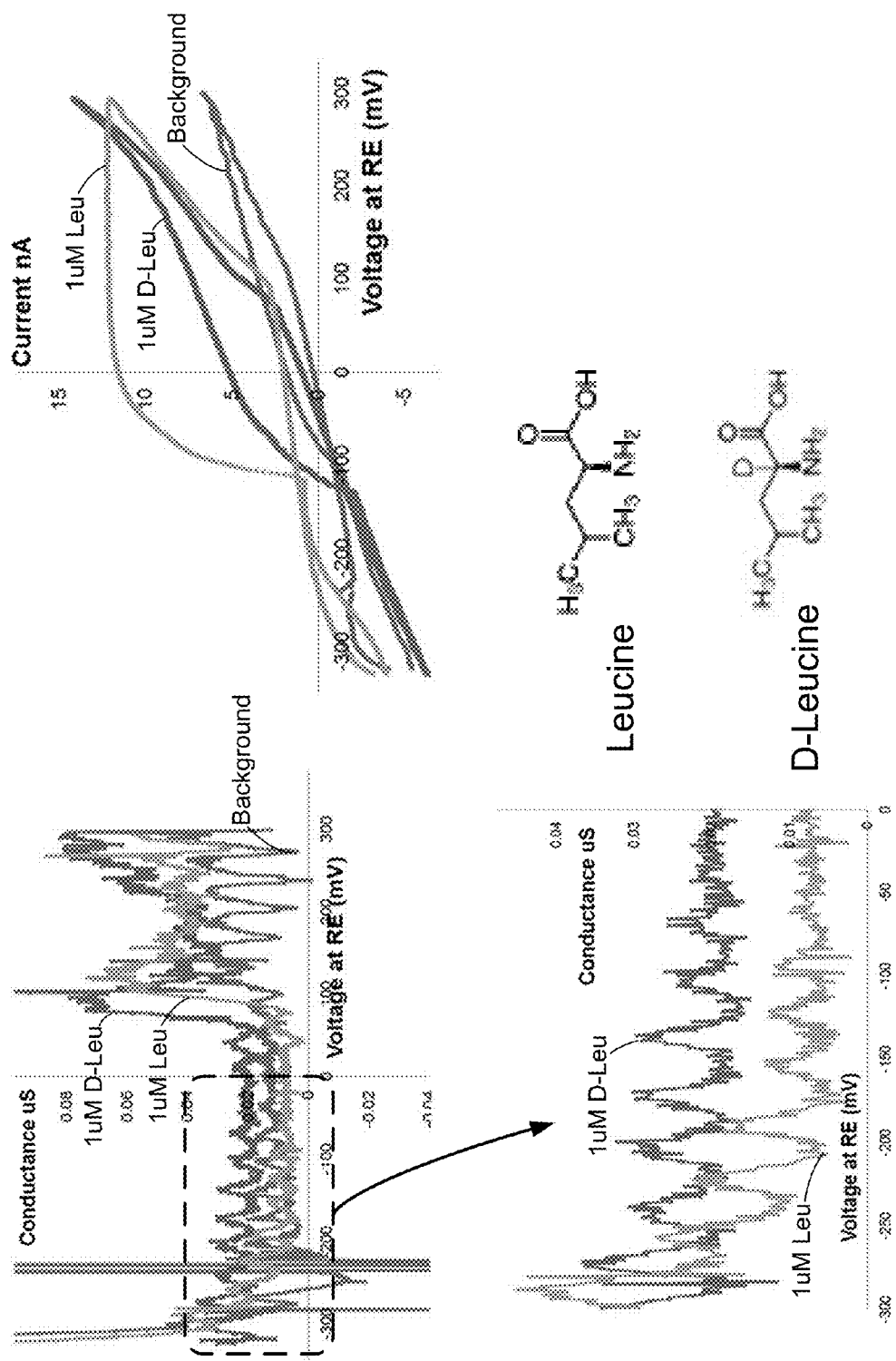
FIG. 5 illustrates example experimental data acquired from a sensing interface representative of the sensitivity of the biosensor described herein to a single atom isotope substitution.

The quantum information transduction mechanism achieved according to the embodiments described herein enables highly specific interrogation of THz frequency molecular vibrations at experimentally accessible (~mV) electronic energies/potentials by scanning the electronic energy with an applied voltage at a metallic, electrically conductive lead. Experimental results, such as those illustrated in FIG. 5, suggest sensitivity of the biosensor described herein to a single atom mass isotope substitution, as well as sensitivity to structural isomerism, which has not been demonstrated before with traditional electronic detection techniques.

Figure 6A:
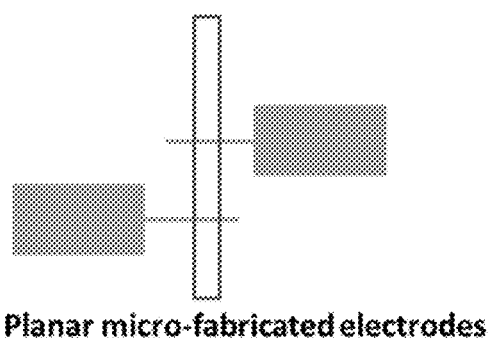
FIGS. 6A-C illustrate example embodiments and geometries of dielectric-film-modified nanoscale electrode-electrolyte interfaces and of nano-engineered interfaces according to aspects of the embodiments.
Figure 6B:
Figure 6C:

According to aspects of the embodiments, various types of biosensor structures and interfaces may be relied upon to specifically optimize electronic and/or electronic-nuclear coupling. For example, various thin (e.g., sub ~1 nm) dielectric-film-modified nanoscale electrode-electrolyte interfaces may be relied upon. The interfaces may be patterned in planar fashion on a silicon die using standard planar microfabrication techniques, for example. FIGS. 6A-C illustrate different types and structures of biosensor interfaces. Depending upon the type of the interface, a liquid or other sample may either be positioned upon or over the interface. Alternatively, the interface may be inserted or immersed in the sample.

Depending upon the type of the biosensor interface, one or more electrodes may be planar with metallic rectangular pads being used for contacts and thin leads being used for the sensing architecture. To control the volume of fluid, a liquid fluidic channel/chamber may be used to contain the volume of liquid sitting atop thin leads of the biosensor interface. In some embodiments, the entire biosensor interface electrode structure may be fabricated on a silicon substrate using standard microfabrication techniques, and the fluidic channel can be made out of a plastic or ceramic and sealed hermetically with the silicon surface to create a leakproof system.

Turning to FIG. 6A, one example of an electrode-electrolyte interface is illustrated. The interface is designed to specifically optimize electronic and electronic-nuclear coupling. In another embodiment illustrated in the example of FIG. 6B, the nanoscale-electrode-dielectric film-electrolyte interface can be localized at the tip of a sharpened probe which may then be inserted into a volume of interest to characterize the spatiotemporal chemistry of the local environment. For the embodiment of FIG. 6B, the tip structure may be fabricated out of an insulator such as glass or plastic, and a thin metal lead is extended to the end of the tip where a sensing electrode exists. In yet another example illustrated in FIG. 6C, leads to electrically address a nano-engineered interface are designed to be "through substrate" rather than planar as mentioned in the first scheme. In this configuration, the substrate is selected to be insulating, like glass, and the design includes aspects of the first and second schemes. It should be appreciated that the example interfaces illustrated among FIGS. 6A-6C are provided by way of example only, and other forms, shapes, and styles of interfaces are within the scope of the embodiments.

According to other aspects of the embodiments described below, using one of the interfaces illustrated in FIGS. 6A-6C, for example, tunneling current flux is recorded by ultra-low noise acquisition circuitry fabricated, for example, by a complementary metal oxide semiconductor (CMOS) process and integrated with the sensing interface using heterogeneous integration or other suitable techniques. According to other aspects of the embodiments, shielding and interconnection topologies are designed to minimize signal contamination caused, for example, by band-limited white noise, electromagnetic interfering signals, flicker noise, and artifacts arising from the digital data acquisition system. Acquired data may be transmitted off-line for further filtering, if necessary, as well as for data recording and display. In certain embodiments, the biosensor further includes means for pre-screening a level of specific biological markers before assaying for an analyte of interest. For example, in a biosensor targeting blood toxins, pre-screening for cytokines allows for evaluation of overall health and can indicate presence or absence of a bacterial infection.

Figure 7:
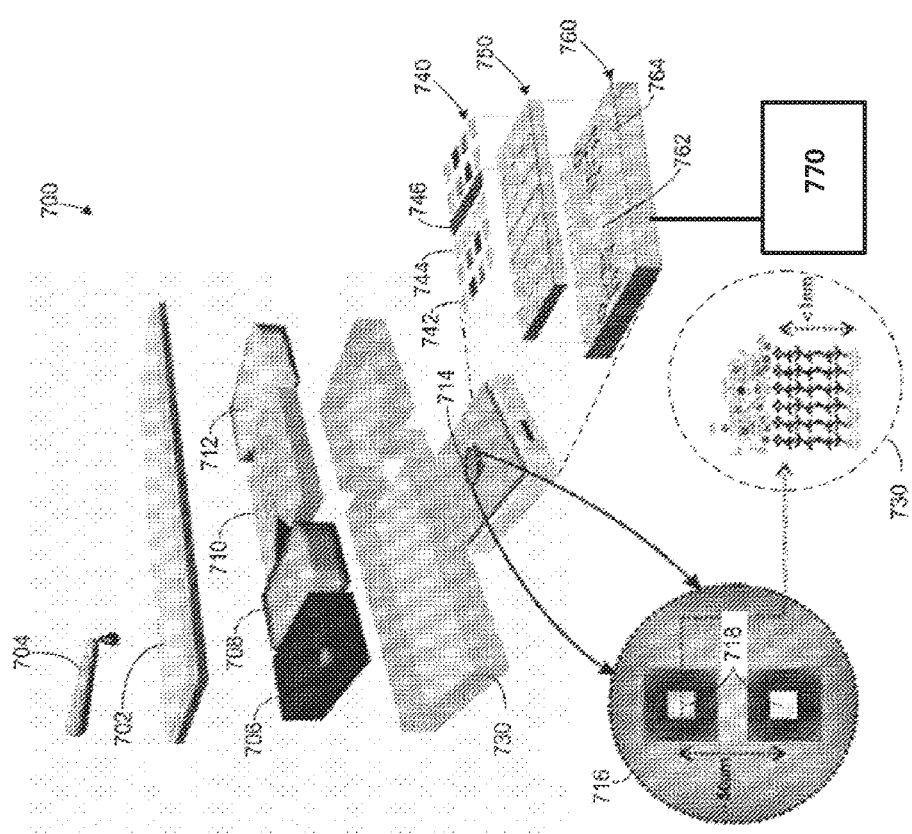
FIG. 7 illustrates an example biosensor platform according to certain aspects of the embodiments described herein.

FIG. 7 illustrates an example biosensor platform 700 according to certain aspects of the embodiments described herein. Among other elements, the biosensor platform 700 includes a fluidic system within a package 730 and a sensor 714. In one embodiment, the fluidic system includes an acquisition zone 702 and one or more disposable modules. The package 730 may allow for easy access to and replacement of the disposable modules. The disposable modules may include a filtration membrane 706, an immunoseparation membrane 708, a micro-chromatograph column 710, and an absorption pad 712, for example, as illustrated in FIG. 7.

In the biosensor platform 700, the sensor 714 may include an electrochemical or patterned electrochemical interface and an interface chip integrated into a low-cost, disposable, lateral flow-based microfluidic architecture. In one example operation, capillary transport may be relied upon in the biosensor platform 700 to separate serum from whole blood and deliver it to an electrode surface of the sensor 714. However, the mechanism to induce fluid flow in the device is not limited to capillary transport or flow. Dielectrophoresis may also be employed to actuate the liquid medium in the portable biochip configuration.

Among other elements, the sensor 714 may include a plurality of thin films 740 (e.g., the electrochemical or patterned electrochemical interface), a semiconductor die 750, and an application-specific integrated circuit (ASIC) 760. The thin films 740 may be deposited by atomic layer deposition, for example, and include working 742, counter 744, and reference 746 films or areas. The semiconductor die 750 may include an electrode array and through-die vias for electrical coupling with the ASIC 760. The ASIC 760 may include bonding pads 762 and 764. The bonding pads 762 may be relied upon for electrical connection with the through die vias from the semiconductor die 750, and the bonding pads 764 may be relied upon for electrical connection to other processing and/or data collection processors or circuitry 770. It should be appreciated, however, that the structure of the sensor 714 illustrated in FIG. 7 is provided by way of example only, as other equivalent structures are within the scope of the embodiments.

In one embodiment, the biosensor platform 700 includes elements at the macro-, micro-, and nano-scales, where the microfluidic elements bridge the nano-scale transducer to blood sampling and dispensing at the macro-scale. Since the patterned sensor interface with the integrated electronic is relatively costly, the microfluidics may be designed such that fabrication costs are relatively low, power consumption is negligible, and the microfluidic component can be easily disposed of if excessive blockage obstructs the flow path.

Referring back to FIG. 7 for a description of the operation of the biosensor platform 700, a sample 704 may be dispersed (e.g., dropped) in the acquisition zone 702. The sample 704 is then either actively (e.g., via dielectrophoresis) or passively (e.g., via capillary action) pumped through the fluidic system. In the example platform in FIG. 7, the sample 704 is first wicked through a filtration membrane 706. In one embodiment, the filtration membrane 706 possesses a graded pore structure capable of separating serum from whole blood. Next the serum passes through the immunoseparation membrane 708, such as a nitrocellulose membrane or other appropriate type of membrane comprising surface antibodies specific to high abundance proteins, which remove the high-abundance proteins. Finally, the liquid sample moves though the micro-chromatograph column 710, thus fractionating the remaining proteins and results in size separated elutants at the exit of the column 710. In one example embodiment, the micro-chromatograph column 710 is comprised of a tapered microfluidic channel containing a photo-polymerized gel.

It is noted that, although not required for all sample types, the fluidic system is preferred when analyzing complex mediums, such as blood, where components may interfere with the detection of low abundance analytes. Pumping of the sample 704 may be active or passive into the fluidic system. It should be appreciated that the filtration media, chosen filter membranes, other membranes, and characteristics of the micro-chromatograph column 710 may be dependent upon factors such as sample type, sample amount, or abundance of target analyte, for example.

Continuing with the operation of the biosensor platform 700 in FIG. 7, after the sample 704 passes through the fluidic system, it is exposed to an active interface at the sensor 714. The active interface includes a transducing electrochemical interface integrated with underlying acquisition electronics, as described herein. An area 716 of the sensor 714 is patterned as electrically accessible, thermally insulated, pixilated electrodes for interrogating the sample 704. It should be appreciated that pixel electrodes 718 of the sensor 714 may be singular or exist as an array in a configuration with common counter and reference electrodes. At 720, FIG. 7 further illustrates a magnified cross section of view of the transducing electrochemical interface with a sample for evaluation disposed thereon.

Figure 8:
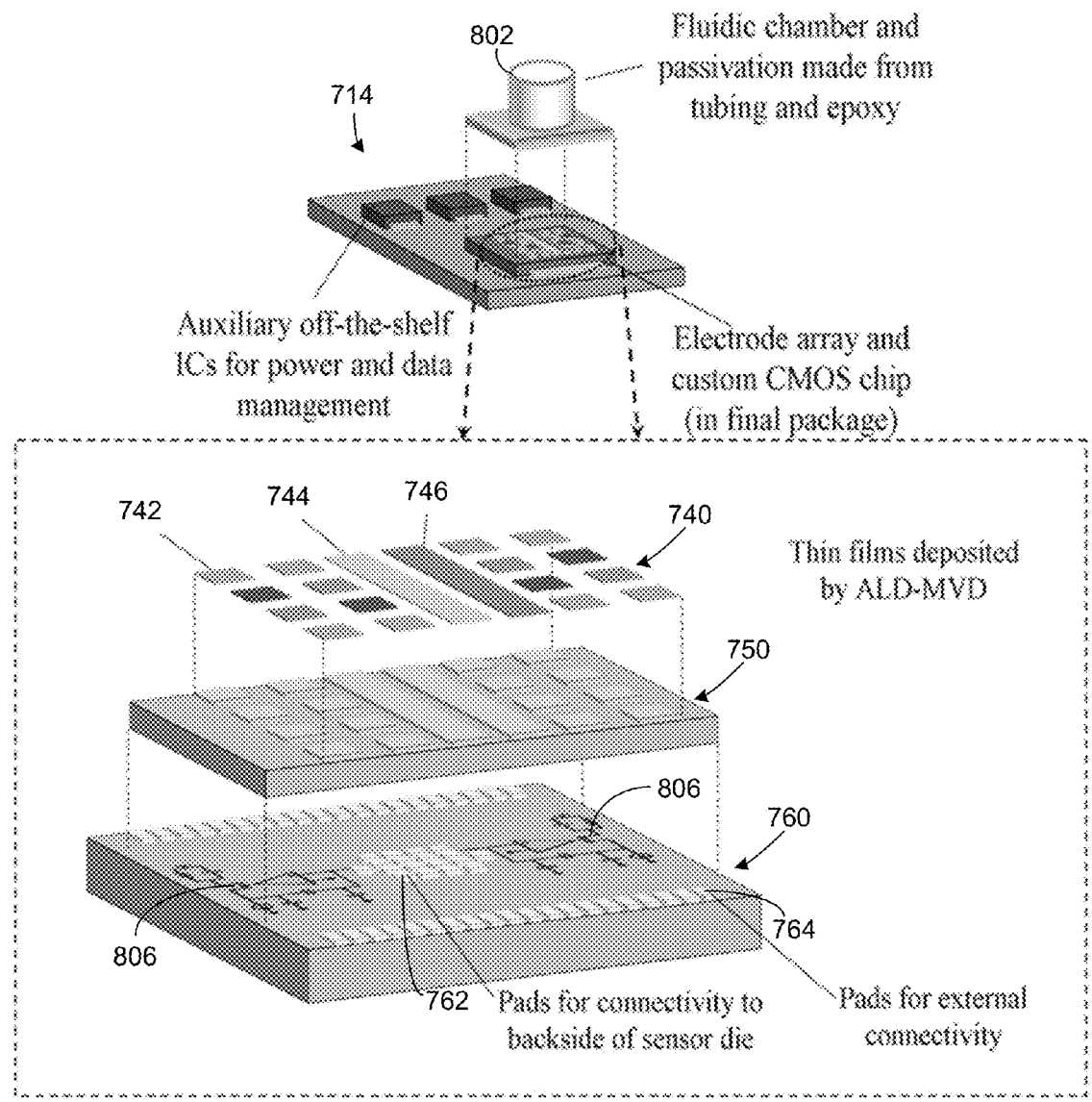
FIG. 8 illustrates an enlarged view of an example sensor with electrodes arranged in an array according to aspects of the embodiments.

FIG. 8 illustrates an enlarged view of sensor 714 with electrode sensors arranged in an array. The sensor 714 in this embodiment exists as a layered, heterogeneously integrated sensor platform. In one embodiment, the sensor 714 includes a fluidic chamber transfer structure 802 that transfers a liquid sample from the fluidic system to the electrode sensor array 804. The sample then reaches the electrochemical interface electrode array of the sensor 714, which includes dielectric thin films deposited by self-assembly techniques, atomic layer deposition, and/or molecular vapor deposition (ALD, MVD). The circuitry 806 of the ASIC 760 may be formed using any suitable semiconductor process including, for example, a CMOS process. The structure and purpose of the circuitry 806 is described in further detail below with reference to FIG. 14.

Referring again to FIG. 7, the biosensor platform 700 may be mounted on a shielded, printed circuit board (PCB) for electrical access. Parallel data acquisition over a large applied bias range is made possible by electronic-energy-window specific optimization of individual electrode pixels, with each electrode pixel nanostructure being optimized for interrogating a specific electronic energy/bias window. If necessary, data acquired as a transition current signal can be transmitted to an external system for post-acquisition processing, storage, and display. The biosensor platform 700 is designed such that sensing and data acquisition modules can be easily added or removed so that the platform can be dissembled, interchanged, and disposed of.

Resolved spectral information, once acquired, is then correlated with vibrational energy data to identify specific molecular species associated with the macro-molecule analyte. This may be accomplished by employing an information-driven strategy for targeted, non-redundant analysis of a bio-analyte in an electrolyte solution. Signatures of information-rich subsets of the bio-analyte, such as cysteine-containing peptides, phosphorylated peptides, or glycosylated peptides, may be tracked in the resolved spectrum of the bio-analyte. These subsets will serve as molecular markers for identifying and quantifying the presence of molecular species of interest. A reference database containing these molecular markers may be constructed for each target analyte as further described below. In other words, each analyte may be expected to produce its own signature spectrum of information. By comparing the resolved spectrum from a sample to the reference database, the target analyte may be identified.

Figure 9:
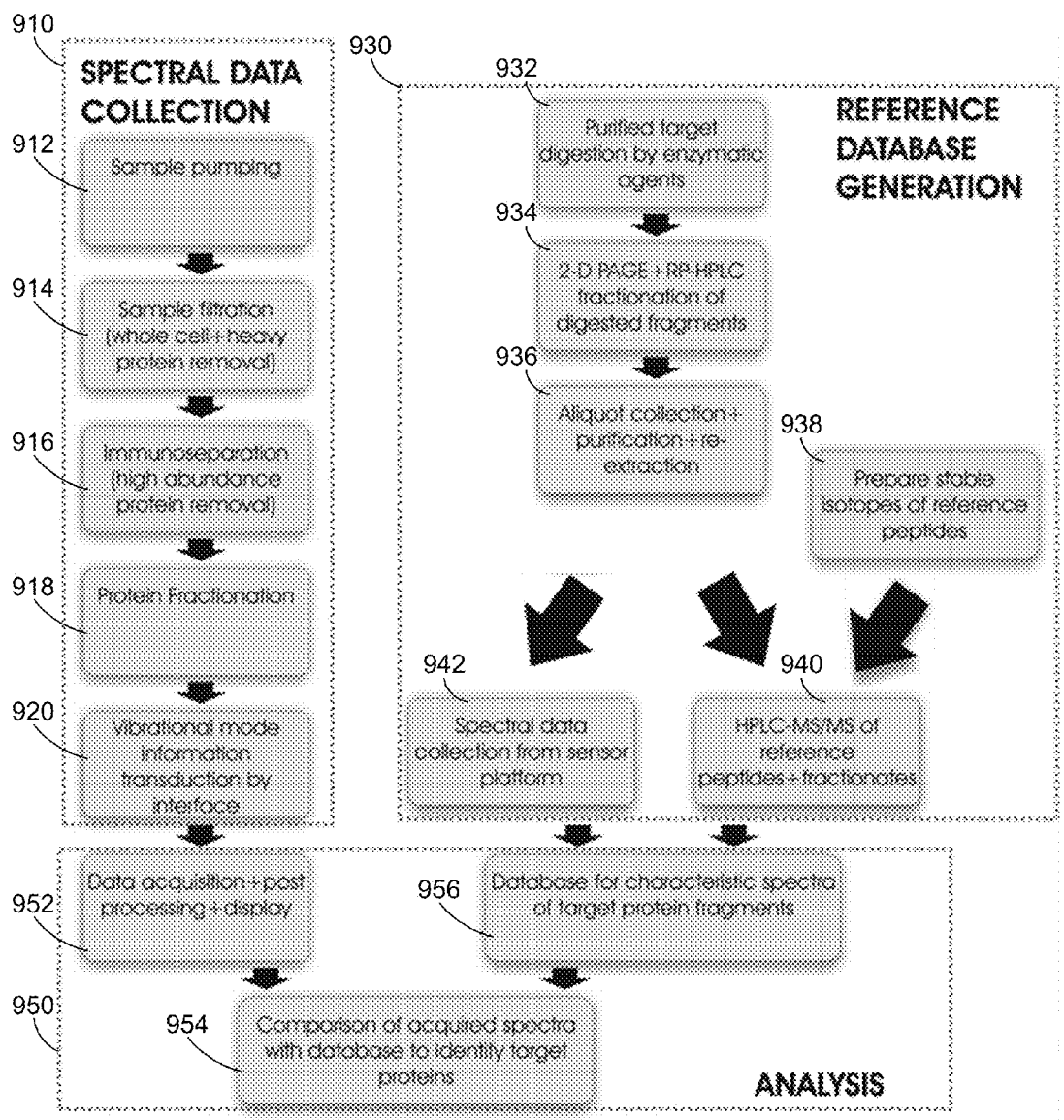
FIG. 9 illustrates processes of spectral data collection, reference database collection, and analysis according to aspects of the embodiments.

Turning to FIG. 9, processes of spectral data collection 910, reference database collection 930, and analysis 950 are described according to aspects of the embodiments. With regard to the process of spectral data collection 910, an example of the process 910 is described below in connection with a sample of raw blood. It should be appreciated, however, that the process 910 may be applied to other types of samples. Further, the process 910 is described below in connection with the biosensor platform 700 of FIG. 7. Again, it should be appreciated that the process 910 may be performed in connection with other biosensor platforms similar to the biosensor platform 700.

Briefly, among other steps, the process of spectral data collection 910 includes pumping a sample through a fluidic system at reference numeral 912, filtering the sample at reference numeral 914, separating and removing at least one composition from the sample at reference numeral 916, fractionating the sample at reference numeral 918, and transducing information from the sample at reference numeral 920. The pumping, filtering, separating/removing, and fractionating, at reference numerals 912, 914, 916, 918, respectively, may be performed in connection with one or more of the disposable modules of the fluidic system described above with reference to FIG. 7. Further, the transducing information at reference numeral 920 may be performed in connection with the sensor 714 described above with reference to FIG. 7.

As for the more particular example of conducting the process of spectral data collection 910 using a sample of raw blood, after pumping at reference numeral 912, the sample of raw blood may be subject to filtering at reference numeral 914, where serum is separated from whole blood. Next, the serum is cleaned of high abundance proteins at reference numeral 916 by passing through an immunoseparation membrane, such as a nitrocellulose membrane that comprises surface antibodies specific to the high-abundance proteins, for example. The liquid sample is then fractionated reference numeral 918, such that different proteins fractions are eluted sequentially onto the active sensor area. The separation of proteins may occur by utilizing a general protein specific property, such as charge-to-mass ratio, to sequentially elute low-abundance proteins. Finally, information is transduced from the eluted proteins at reference numeral 920.

FIG. 9 further illustrates the process of reference database collection or generation 930. As one example embodiment of the process 930, at reference numeral 932, the process 930 includes digesting a purified recombinant form of a target molecule (or biological surrogate, in the case of neurotoxins). That is, the target molecule is systematically digested by enzymes, such as trypsin and chymotripsin, to generate peptide fragments. At reference numeral 934, the digesting is followed by separating using a multi-dimensional separation technique, such as a 2-D poly acrylamide gel electrophoresis (2-D PAGE) process in tandem with high performance liquid chromatography (HPLC, preferably reverse phase-HPLC), for example. At reference numeral 936, the process 930 includes collecting fractions. That is, fractions are collected, purified, and re-extracted in a suitable buffer and analyzed using the disclosed quantum tunneling electronic biosensor at reference numeral 942. The data, after background subtraction, is analyzed for characteristic spectra of moieties specific to the peptide fragment in the aliquot being tested.

In other aspects of the process 930, stable isotopes of reference peptides, for example, may also be prepared at reference numeral 938. In some embodiments, the same fractions as well as isotope-labeled reference peptides prepared at reference numeral 938 may also be examined in parallel by traditional liquid chromatography-mass spectrometry (HPLC-MS-MS) techniques at reference numeral 940.

The analysis process 950 may include, at reference numeral 952, one or more of acquiring, post processing, and/or displaying data collected by the spectral data collection process 910. At reference numeral 954, the analysis process 950 may also include comparing signatures from the data collected by the spectral data collection process 910 with a database of reference signatures (i.e., 956) collected by the reference database collection process 930. At reference numeral 954, the database of reference signatures 956 may be compared with raw data from the biosensor platform 700 to identify molecular analytes of interest. It should be appreciated that the processes 910, 930, and 950 are provided by way of example only.

Figure 10:
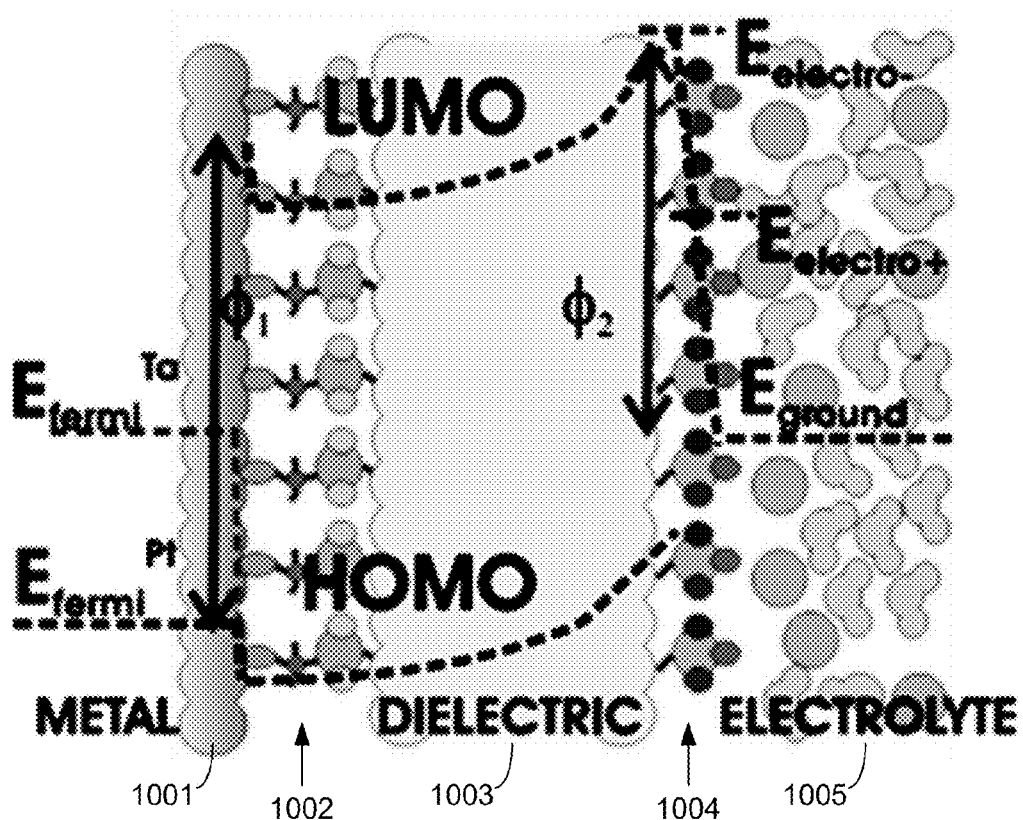
FIG. 10 illustrates example tunneling barriers at metal-dielectric and dielectric-electrolyte interfaces according to aspects of the embodiments.

Turning to FIG. 10, example tunneling barriers at metal-dielectric and dielectric-electrolyte interfaces are further described according to aspects of the embodiments. In some embodiments, the tunneling barriers can be engineered utilizing thin films, such as those included in the sensor 714 of FIG. 4, of organic or inorganic materials with suitable properties to minimize the electronic coupling between the energy levels of the electrode and redox active species in the electrolyte. FIG. 10 depicts tunneling barriers $\phi_1$ and $\phi_2$ at the metal-dielectric 1002 and dielectric-electrolyte 1004 interfaces. Coupling between initial and final electronic energy states in the optimally coupled electronic transition is modulated by an electrostatic tunneling barrier $\phi_2$ located at the dielectric-electrolyte interface 1004 as well as by an effective barrier limiting charge injection at the electrode-dielectric interface 1002. Nanoscale engineering of barrier heights at the electrode-dielectric thin-film interface 1002 as well as at the dielectric thin-film-electrolyte interface 1004 is utilized to minimize de-phasing of resonant signatures of energy exchange in the electronic transition due to strong electronic coupling.

The desired minimization may be achieved by increasing the electron-tunneling barrier $\phi_2$ at the dielectric-electrolyte interface. In one embodiment, the electron tunneling barrier $\phi_2$ increases as the electrolyte pH increases. Other exemplary embodiments achieve an increased tunneling barrier by increasing electrolyte anion electronegativity, increasing dielectric monolayer functional group electronegativity, and/or increasing dielectric monolayer thickness, for example.

The desired minimization in electronic coupling may also be attained by increasing the limiting barrier $\phi_2$ at the dielectric-electrolyte interface 1004. In one embodiment, this is achieved by coating the dielectric monolayer 1003 with an organic coating, such as short chain silanes, with different electronegative, electrolyte-facing functional groups, such as —OH, —OR, —COOH, —SH, —SR, —COR, —NO2, —Br, or the like. These aforementioned coatings are suitable for forming with MVD at the dielectric surface 1003.

The metal electrode-dielectric barrier 1002, unlike the dielectric-electrolyte barrier 1004, is a function of the metal work-function, dielectric band gap, and nature of molecular orbital distortion induced by a bond between the metal 1001 and dielectric materials 1003. A reduction in the coupling between electrode 1001 and electrolyte 1005 may also be achieved by altering the tunneling barrier located at the dielectric-electrode interface. For example, increasing the tunneling barrier $\phi_1$ at the dielectric-electrode surface reduces coupling between electrode and electrolyte phases, thus leading to increased resolution of vibrational frequency information in the measured current.

For some embodiments, the mechanism of tunneling based charge injection in the dielectric 1003 would be electron tunneling. In other words, the dielectric 1003 would be comprised of an inorganic-oxide. For these embodiments, metals such as Pt, Ir, Se, or Au, or their alloys in different compositions are preferred. For other embodiments, hole-tunneling is the mechanism of charge injection in the dielectric 1003. It should be appreciated that the dielectric or dielectric film 1003 in these embodiments may be comprised of an organic alkane. For these embodiments, metals like Ta, Ti, Zr, Hf, or their alloys in various compositions may be preferred. The final metal choice is dependent on many factors including mechanical, diffusional, and electrochemical stability of the electrode, ease of deposition, electrical resistivity, and ability to seed a dielectric layer, for example.

Among embodiments, nanoscale structures of metal electrodes for sensors described herein are fabricated either in top-down methods using nanoscale patterning techniques like Electron Beam Lithography (EIB) or Focused Ion Beam (FIB), or bottom-up methods like nanoparticle self-assembly on patterned structures or using a combination of methods thereof.

In various embodiments, the dielectric film 1003 that spatially separates the electrode 1001 and electrolyte 1005 layers is comprised of a medium-k nanolaminate. The high-k material in this nanolaminate may be $Ta_2O_2$, $ZrO_2$, $TiO_2$ or other suitable material. It is noted that large dielectric constants for the insulating film facilitate greater charge accumulation at the dielectric-electrolyte interface, thus effectively increasing the tunneling barrier and reducing the electronic coupling. However, the increased charge density increases the nuclear-electronic coupling. Also, since a larger dielectric constant is typically associated with small band-gap and, consequently, higher non-tunneling leakage current, the high-k material may be intercalated between alternating layers of lower-dielectric constant oxides.

Figure 11:
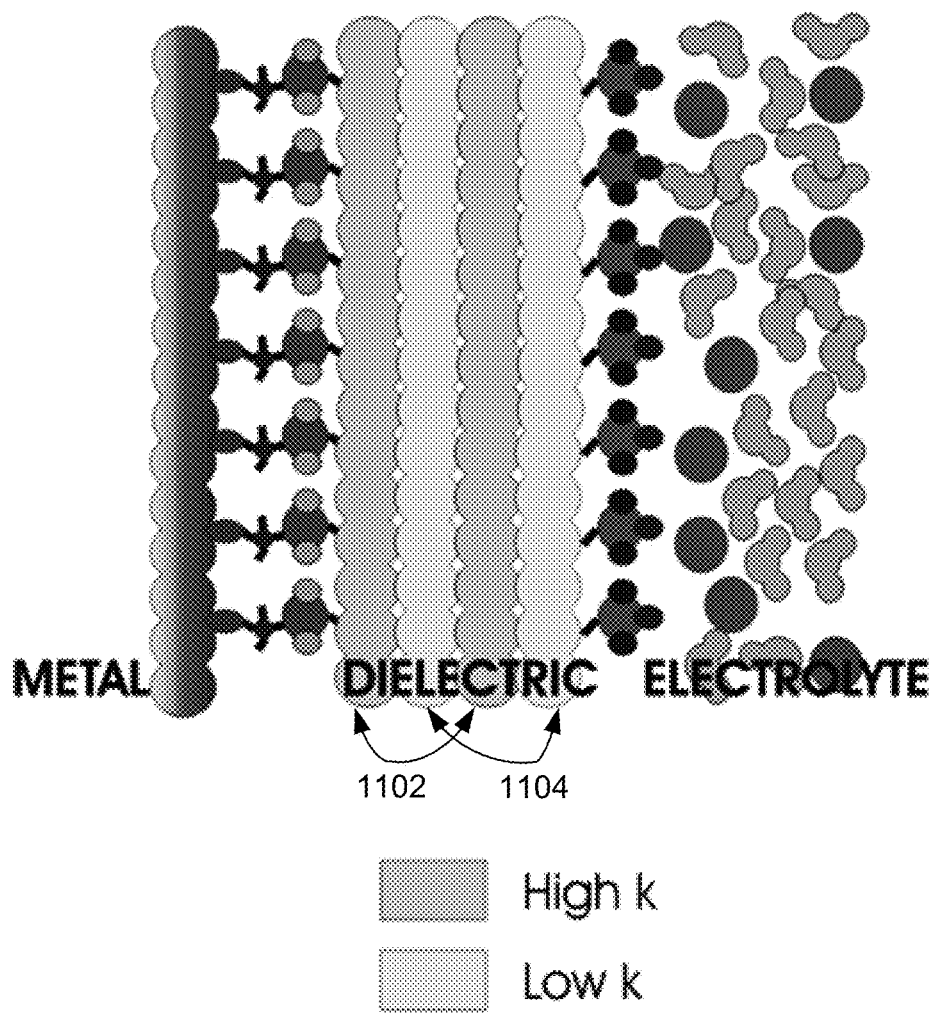
FIG. 11 illustrates sequential layering of high and low k-dielectric materials for a high-k dielectric insulator according to aspects of the embodiments.

In the context outlined above, FIG. 11 illustrates sequential layering of high 1102 and low 1104 k-dielectric materials for a high-k dielectric insulator according to aspects of the embodiments. The final choice of materials used to form a given dielectric nanolaminate may be determined by insulator properties like breakdown resistance, electrochemical and mechanical stability, and chemical inertness to aqueous electrolytes in the presence of an applied bias. Other low-k materials, like molecular organic spacers (e.g., derivatized alkane/alkene thiols and derivatized silanes) may also be used as functional insulating spacers for the nanoscale interface, for example.

On the other hand, the dielectric film utilized to insulate the addressing lead from the electrolyte solution would typically be of low-k material like SiO2. The low-k nature of the insulating dielectric would minimize losses induced by the parasitic capacitance that contributes to the dephasing of the resonance signal. The sensor interface configuration may thus be comprised of low-k and high-k insulating material co-patterned on the same interface depending on the functional utility of the insulator.

Reduction in nuclear-electronic coupling may, additionally or alternatively, be achieved by applying a directional magnetic field to the nanoscale electrochemical interface, where a) the dielectric film that serves as the function insulating element includes a nanolaminate structure that uses differentially oriented film magnetic moments to constrain the spin of the tunneling electron, and b) the nanoscale electrode participating in the redox reaction would comprise a nanostructured ferromagnetic/paramagnetic element with strongly oriented electronic moments. Preferably, the magnetic tunneling nanolaminate will comprise dielectric-based thin-film architectures with room temperature ferromagnetic properties that allow for the generation of local, inhomogeneous magnetic fields that can interact with the magnetic dipole of the transitioning electron to "gate" the quantum-mechanical transition.

Figure 12:
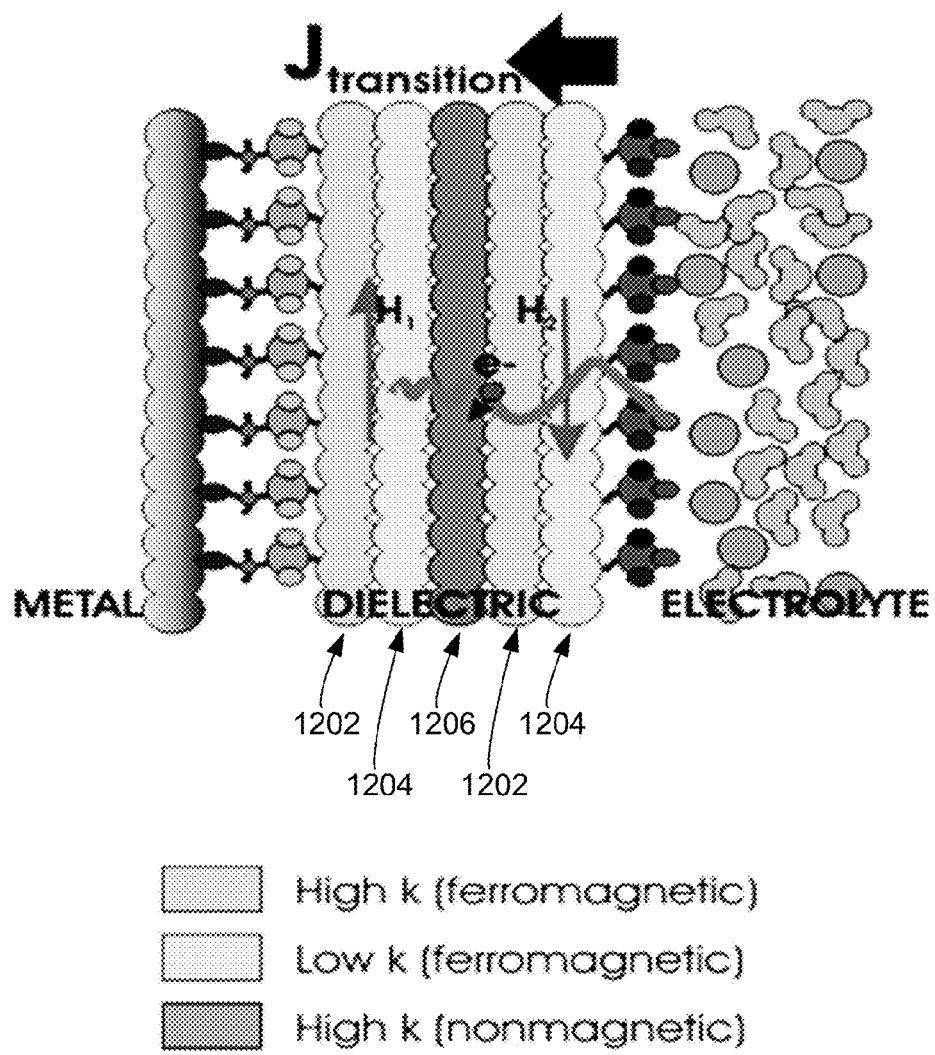
FIG. 12 illustrates a magnetic tunneling film architecture that uses differentially oriented film magnetic moments to further restrict electronic transition according to aspects of the embodiments.

In the context outlined above, FIG. 12 illustrates a magnetic tunneling film architecture that uses differentially oriented film magnetic moments to further restrict electronic transition according to aspects of the embodiments. A multistage-gate-like design of the dielectric nanolaminate may enable further minimization of the de-phasing resulting from nuclear-electronic coupling between the energy of the tunneling and the surrounding bath of thermal vibrations. In one embodiment, the dielectric film includes low-k (e.g., $HfO_2$) 1204/high-k 1202 dielectric substacks interspersed with thin films of a non-magnetic dielectric insulator 1206 with an intermediate value of dielectric permittivity, such as Al2O3. Aluminum in the $Al_2O_3$ thin-film lack the d-shell orbitals necessary for displaying magnetic susceptibility and thus the alumina thin-films are believed to be non-magnetic, making them suited for this application. In other words, the functional ferromagnetic elements of the dielectric thin film are made up of low-k (e.g., $HfO_2$) 1204/high-k 1202 dielectric substacks and every two subs-stacks are separated by $Al_2O_3$ thin-film which functions as an insulating barrier that minimizes dissipative magnetic coupling between adjoining ferromagnetic sub-stacks. The total number of substacks and $Al_2O_3$ thin-films and, thus, the extent of ferromagnetic-induced decoupling, is limited by the overall thickness of the dielectric film, which is less than approximately 10 nm in various embodiments.

Figure 13A:
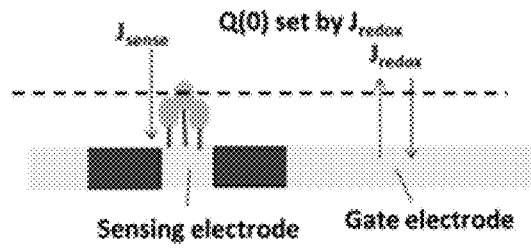
FIGS. 13A-C illustrate example embodiments of gate-electrode systems according to aspects of the embodiments.

Further reduction in nuclear-electronic coupling may be made possible by the application of a "reaction" gate to control the interface charge density at the electrochemical interface. The electrochemical reaction gate proposed in this embodiment would utilize a fast/adiabatic electrochemical electron transfer reaction to set the charge density across the entire solid-liquid interface, which would also include a small sensing interface area, as illustrated in the example of FIG. 13A. The interface charge control mechanism in this case is referred to as an electrochemical reaction gate because, like a traditional metal oxide semiconductor (MOS) gate structure, the reaction gate uses an applied voltage (independent of sensor biasing voltage) to control the charge density at the interface. However, unlike a traditional MOS gate, the reaction gate relies on a fast electrochemical charge transfer reaction to set the surface charge density to the desired optimal value to ensure an optimal level of electronic and electronic-nuclear coupling. This embodiment of the sensor interface may be advantageous in that it decouples the modulation of the interface charge density from the sensing function, and facilitates an independent modulation of the coupling mechanisms that can dephase the electronic resonances. The dimensions of the sensing and gate electrode regions may be settled upon based on the design rules described herein. In this embodiment, the gate voltage and the voltage applied to cause the sensing electronic transition are independent. However, the electrochemical reaction causing the gating effect utilizes the same redox-active species in the electrolyte as the sensing interface.

Figure 13B:
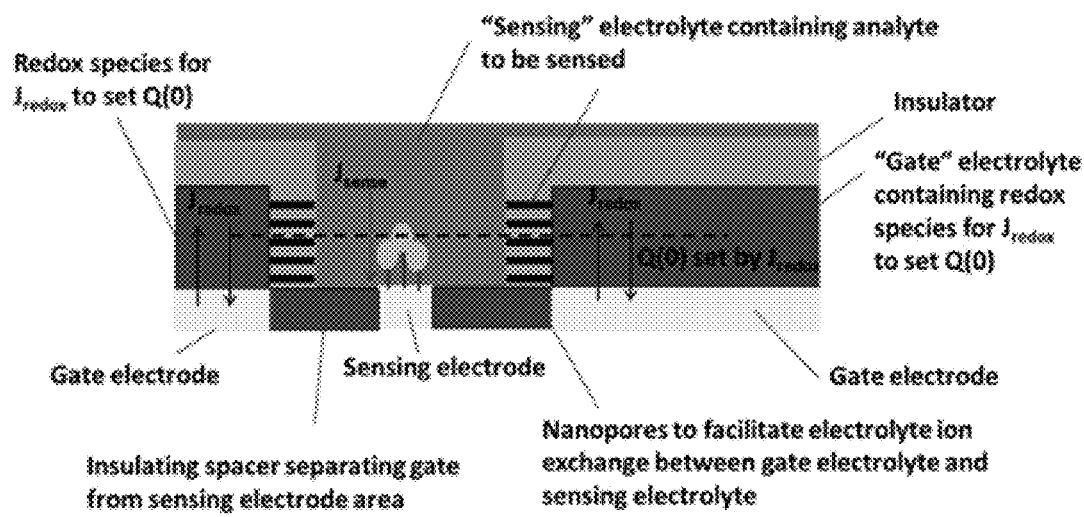

In yet another example embodiment of the gate-electrode system, as illustrated in FIG. 13B, the interface is configured to ensure that the gate control is substantially or completely decoupled from the sensing function, where the electrolyte and redox active species responsible for the fast/adiabatic reaction that sets the interface charge density are encapsulated in a fabricated nanofluidic structure that reduces the mass and ion exchange with the sensing electrolyte containing the analyte to be sensed. The nanofluidic structure, however, permits electrical connectivity between the "gating electrolyte" and "sensing electrolyte" and, therefore, a uniform or near-uniform interface charge density may be set across the entire solid liquid interface. The nanofluidic structure described allows for the inter-diffusion of small ionic species like protons and hydroxyl radicals between the gating electrolyte and the sensing electrolyte, while sterically blocking and preventing contamination by the larger redox active ions.

Figure 13C:
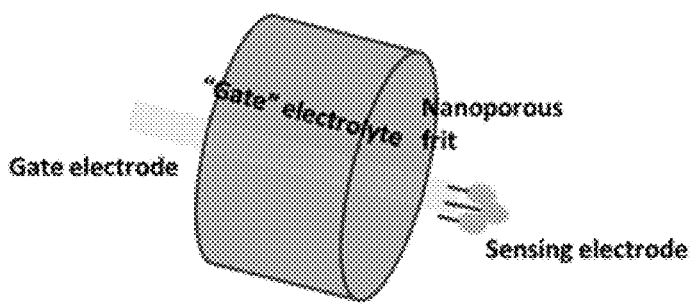

A third embodiment of the gate-controlled sensing interface would consist of the sensing interface being localized on the tip of a sharpened probe, with the gate electrode being co-located on the body of the probe. As illustrated in the example of FIG. 13C, the gate and sensing regions of the device may be segregated by a nanoporous frit filter that allows for electrical communication between the gating electrolyte and the sensing electrolyte.

Another key component to the biosensor platform 700 (FIG. 7) is the analog front-end instrumentation, which is relied upon for conditioning voltage signals to measure vibrational frequency signatures in the electrochemical tunneling current. The conditioning of the applied voltage signals involves utilizing a relatively large gain feedback loop to minimize and set the noise present at the electrochemical interface to a predetermined value. The noise at the electrochemical interface may be due to physical or electronic sources present either at the interface or in the measurement instrumentation respectively. The physical sources of noise are correlated positively with the parameters that promote increased electronic and electronic-nuclear coupling and therefore, manipulation of physical noise at the electrochemical interface enables direct and active control of the coupling effects. By contrast, engineering of the physical interface, as described herein, is a passive control on the coupling mechanisms.

Besides physical sources of noise, electronic sources of noise from the measurement instrumentation (e.g., wide band thermal noise, wideband shot noise, 1/fα noise, etc.) also manifest across the electrochemical interface and may manifest as enhanced coupling. Therefore, electronic instrumentation should be designed to minimize electronic noise and to set the physical noise to pre-determined, desired levels.

The measured non-adiabatic current is a function of two non-interacting frequency domains: (a) a "macro-frequency" (approximately 1 Hz) that determines the rate-limiting step in the macroscopic electrochemical system and (b) a "micro frequency" ($>10^{12}$ Hz) that measures the dynamics of molecular vibrations and the tunneling process, where the dynamics are manifest in the electronic energy (or equivalently, the applied bias) space. Multiple measurement schemes involving different voltage signal types and differing forms of data acquisition are proposed for the identification of signatures in the measured current.

In one case, a small amplitude low-frequency Alternating Current (AC) voltage excitation is combined with a Direct Current (DC) voltage bias and applied to the electrochemical interface. Then, the lock-in acquired AC current is recorded as a function of Direct Current (DC) bias at the nano-engineered electrode-electrolyte interface. In another case, a DC voltage is applied directly to interface and a DC current is acquired. In still another case, a small amplitude low frequency AC voltage is combined with a DC bias and applied at the interface and higher harmonics of the measured current are acquired with lock-in techniques. The application of the DC and AC voltages and simultaneous acquisition of the current may be accompanied by the automated modulation of applied magnetic fields or noise power set-points. Effective signal extraction requires suppression of extrinsic noise contributions and control of intrinsic noise contributions. The acquisition of the tunneling current signal (AC and DC components) requires implementation of suitable hardware and software-based data filtration techniques to minimize electronic noise picked up in the measurement process.

Figure 14:
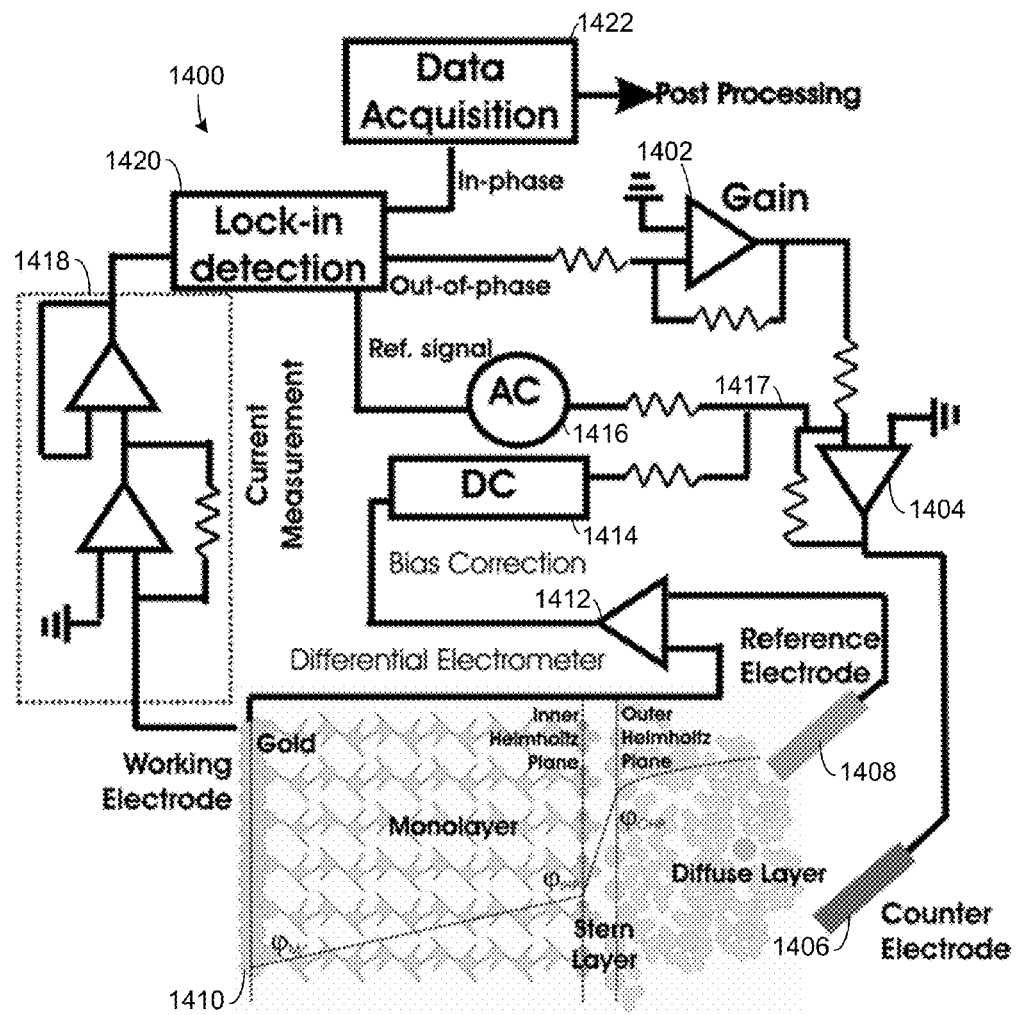
FIG. 14 illustrates an example of three-electrode feedback suppression of thermal noise for electronic transition measurements according to aspects of the embodiments.

Turning to FIG. 14, an example of three-electrode feedback suppression of thermal noise for electronic transition measurements is illustrated according to aspects of the embodiments. In FIG. 14, a three-electrode analog measurement topology is used with high gain feedback incorporated to suppress the voltage-noise in the macro-frequency domain. Current is acquired with a transimpedance amplifier topology, where the tunneling current flowing across a resistor is converted into a voltage that is measured. Set values of passive components in the transimpedance amplifier signal chain allow for the measurement of AC or DC currents. Within this embodiment, the instrumentation system can apply a low noise voltage (DC, DC+AC) and measure AC or DC currents. Real and imaginary components (i.e., resistive and capacitive current contributions, respectively) of the measured AC current or higher harmonics of the signal can be isolated using traditional lock-in detection techniques.

Thus, with reference to FIG. 14, a three-electrode analog measurement topology circuit 1400 may be used for high gain feedback suppression of voltage-noise in the macro-frequency domain. The circuit 1400 includes a first gain amplifier 1402, a second gain and summing amplifier 1404 coupled to an output of the first gain amplifier 1402, and a counter electrode 1406 coupled to an output of the second gain amplifier 1404. The circuit 1400 further includes a reference electrode 1408 and a working electrode 1410, each coupled to a difference amplifier 1412. An output of the difference amplifier 1412 is coupled to a DC generator 1414. Outputs of the DC generator 1414 and an AC generator 1416 are combined at a node 1417 in the circuit 1400 and provided as an input to the second gain amplifier 1404. As illustrated in FIG. 14, the combined outputs of the DC and AC generators 1414 and 1416 are further combined with the output of the first gain amplifier 1402 at the node 1417 before being provided as input to the second gain amplifier 1404.

The circuit 1400 further includes a current measurement circuit 1418 coupled to the working electrode 1410 and a lock-in detection circuit 1420 coupled to an output of the current measurement circuit 1418. As illustrated in FIG. 14, a reference signal output of the lock-in detection circuit 1420 is provided as an input to the AC generator 1416, an out-of-phase signal output of the lock-in detection circuit 1420 is provided as an input to the first gain amplifier 1402, and an in-phase signal output of the lock-in detection circuit 1420 is provided as an input to a data acquisition element 1422 for processing.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

Further, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

At least the following is claimed:

1. A biosensor platform system, comprising:
   a tunneling biosensor interface configured to operatively couple to a fluidic system configured to receive a sample comprising a redox specie and an analyte specie, the tunneling biosensor interface comprising:
   a transducing electrode array comprising at least one dielectric thin film deposited on an electrode array and configured to contact the sample, wherein the at least one dielectric thin film comprises a sequential layering of low-k and high-k dielectric materials; and
   processing logic operatively coupled to the transducing electrode array, and configured to apply a voltage bias between the received sample and the transducing electrode array, the applied voltage bias configured to generate a tunneling current configured to flow from the redox specie to the transducing electrode array via the at least one dielectric thin film,
wherein the tunneling current is indicative of the analyte specie.

2. The biosensor platform system of claim 1, wherein the fluidic system comprises at least one of:
   a sample acquisition zone;
   a filtration module in fluidic communication with the sample acquisition zone;
   an immunoseparation module in fluidic communication with the filtration module;
   a tapered micro-chromatogram in fluidic communication with the immunoseparation module; and
   an adsorption pad in fluidic communication with the tapered micro-chromatogram.

3. The biosensor platform system of claim 1, wherein the at least one dielectric thin film comprises a sequential layering of low-k and high-k dielectric substacks interspersed with thin films of a non-magnetic dielectric insulator.

4. The biosensor platform system of claim 1, wherein the processing logic includes a low noise transimpedance amplifier configured to detect the tunneling current.

5. The biosensor platform system of claim 1, wherein the tunneling current is indicative of molecular vibrational states of the analyte specie located at the biosensor interface.

6. A biosensor platform system, comprising:
   a fluidic system configured to receive a sample comprising a redox specie and an analyte specie;
   a biosensor interface including dielectric thin films layered on an electrode array on a semiconductor die, wherein the dielectric thin films comprise tunneling barriers at metal-dielectric and dielectric-electrolyte interfaces; and
   processing logic operatively coupled to the biosensor interface, and configured to apply a voltage bias between the received sample and an electrode in the electrode array, the applied voltage bias configured to generate a tunneling current configured to flow from the redox specie to the electrode array via the dielectric thin films,
   wherein the tunneling current is indicative of the analyte specie.

7. The biosensor platform system of claim 6, wherein the processing logic is coupled to the electrode array by through-silicon vias in the semiconductor die.

8. The biosensor platform system of claim 6, wherein the fluidic system comprises at least one of:
   a sample acquisition zone;
   a filtration module in fluidic communication with the sample acquisition zone;
   an immunoseparation module in fluidic communication with the filtration module;
   a tapered micro-chromatogram in fluidic communication with the immunoseparation module; and
   an adsorption pad in fluidic communication with the tapered micro-chromatogram.

9. The biosensor platform system of claim 6, wherein the processing logic comprises a voltage source to apply the voltage bias, and the applied voltage bias is further configured to produce a weakly-coupled non-adiabatic electron flux across a transducing electrode array of the biosensor interface.

10. The biosensor platform system of claim 6, wherein the dielectric thin films comprise a sequential layering of low-k and high-k dielectric materials.

11. The biosensor platform system of claim 10, wherein the high-k dielectric materials comprise at least one a material selected from the group consisting of:
    $Ta_2O_2$;
    $ZrO_2$, and
    $TiO_2$.

12. The biosensor platform system of claim 10, wherein the low-k dielectric materials comprise one of HfO2 and SiO2.

13. The biosensor platform system of claim 6, wherein the dielectric thin films comprise a sequential layering of low-k and high-k dielectric substacks interspersed with thin films of a non-magnetic dielectric insulator.

14. The biosensor platform system of claim 6, wherein the dielectric thin films comprise a nanolaminate structure of differentially oriented magnetic moment films.

15. The biosensor platform system of claim 14, wherein the nanolaminate structure comprises layers of a non-magnetic dielectric insulator intercalated between alternating sub stack layers of a first high-k dielectric ferromagnetic material and a second low-k dielectric ferromagnetic material.

* * * * *